April 6, 1971 P. DICKSON Plant Pat. 3,037
ROSE PLANT
Filed May 2, 1969
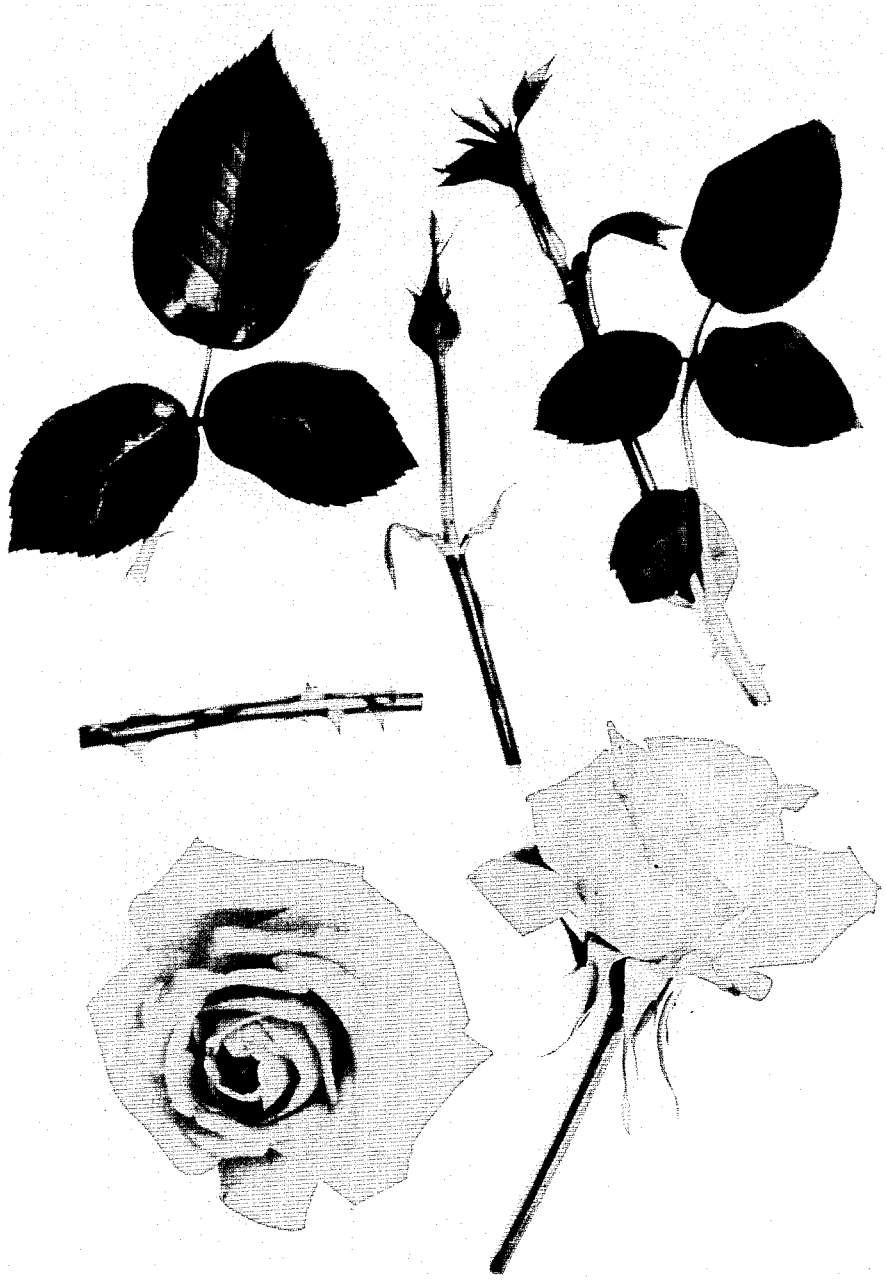
Inventor.
Patrick Dickson
By: Robb & Robb
Attorneys.

United States Patent Office

Plant Pat. 3,037

Patented Apr. 6, 1971

3,037

ROSE PLANT

Patrick Dickson, Newtownards, Ireland, assignor to Jackson & Perkins Company, Newark, N.Y.

Filed May 2, 1969, Ser. No. 821,514

Int. Cl. A01h *5/00*

U.S. Cl. Plt.—20 1 Claim

The present invention relates to a new and distinct variety of rose plant of the hybrid tea class, which was originated by me by crossing the rose variety known as "Silver Lining" (unpatented) with the rose variety known as "Prima Ballerina" (unpatented).

The primary objective of this breeding was to produce a new and improved rose variety of the hybrid tea class which bears attractive and well formed double flowers of red color on a vigorous and well-branched plant. This objective was fully achieved, along with other desirable features, as evidenced by the following unique combination of characteristics which are outstanding in the new variety and which distinguish it from its parents, as well as from all other rose varieties of which I am aware:

(1) A vigorous, upright and well branched plant habit;

(2) An abundance of dark green, glossy foliage which is relatively resistance to blackspot and powdery mildew;

(3) Large, double flowers having from 60 to 70 petals and which open to a high-centered flower form; and (4) A distinctive and attractive light red general color tonality of the flowers, with the color being lighted in shade on the reverse sides of the petals than on their upper sides.

Asexual reproduction of my new rose variety by budding, as performed at Newark, N.Y., U.S.A., and also at Livermore, Calif, U.S.A. shows that the aforementioned characteristics come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Robert F. Wilson's Horticultural Colour Chart (1941), except where general color terms of ordinary dictionary significance are obvious:

Parentage: Seedling of "Silver Lining"×"Prima Ballerina."

Classification:

*Botanical.*—Rosa hybrid.

*Commercial.*—Hybrid tea.

Propagation: Holds its distinguishing characteristics through succeeding propagation by budding.

*Flower*

(Observations made from specimens grown in a greenhouse at Newark, N.Y., U.S.A., in the morning, late in the month of March.)

Blooming habit: Recurrent—continuous.

Bud:

*Size.*—Large.

*Form.*—Urn-shaped.

*Color.*—When sepals first divide—between Rose Red, Plate 724 and Chrysanthemum Crimson, Plate 824. When half-blown—inside of petals: Rose Red, Plate 724/1, reverse of petals: Tyrian Rose, Plate 24/2.

*Sepals.*—Serrated, with 2 lightly branched.

Color—inside: Scheele's Green, Plate 860/3, covered with white tomentum. Outside: Spinach Green, Plate 0960/1.

*Receptacle.*—Color—Scheele's Green, Plate 860. Shape—funnel. Size—large. Surface—smooth.

*Peduncle.* — Length — medium. Surface — prickly. Strength—stiff; erect. Color—Scheele's Green, Plate 860.

*Opening.*—Generally slow opening; slight quilling of outer petals.

Bloom:

*Size.*—Large.

*Borne.*—Singly.

*Stems.*—Long.

*Form.*—High-centered; semi-globular; retains its form to the end.

*Petalage.*—Number of petals under normal conditions—from 60 to 70.

*Color.*—Center of flower—Rose Red, Plate 724/1 on inside of petals and Tyrian Rose, Plate 24/2 on reverse of petals.

Outer petals—inside of petals—Rose Red, Plate 724/1. Reverse of petals—Tyrian Rose, Plate 24/2. Base of petals—small area of Mimosa Yellow, Plate 602/1 at base. General tonality from a distance—Rose Red, Plate 724/1.

*Discoloration.*—General tonality at end of first day—Rose Red, Plate 724/1. Third day—Between Chrysanthemum Crimson, Plate 824/3 and Tyrian Purple, Plate 727.

Petals:

*Texture.*—Leathery; thin.

*Surface.*—Inside—satiny; reverse—satiny.

*Shape.*—Oval.

*Form.*—Edges slightly quilled.

*Arrangement.*—Imbricated.

*Petaloids in center.*—Few.

*Persistence.*—Drop off cleanly.

*Fragrance.*—None.

*Lasting quality.*—On the plant—very long. As cut flower—long.

Reproductive organs:

*Anthers.*—Medium size; many; regularly arranged around styles. Color—Yellow.

*Filaments (threads).*—Medium length. Color—Reddish brown.

*Styles.*—Bunched; uneven length; short.

*Stigmas.*—Color—White.

*Fruit.*—None observed.

*Plant*

Form: Bush.

Growth: Very vigorous.

Foliage: Compound of 5 leaflets.

*Size.*—Large.

*Quantity.*—Abundant.

*Color.*—New foliage: Oxblood Red, Plate 00823. Old foliage: upper side—Parsley Green, Plate 00962. Under side—Spinach Green, Plate 0960.

*Shape.*—Oval pointed.

*Texture.*—Upper side—glossy; under side—smoooth.

*Ribs and veins.*—Ordinary.

*Edge.*—Serrated.

*Serration.*—Double.

*Petiole.—Rachis*—Same green color as upper and reverse sides of leaf. Underside—Prickly.

*Stipules.*—Short.

*Disease resistance.*—Relatively resistant to blackspot and powdery mildew, as determined by comparison with other varieties grown under the same conditions at Newark, N.Y., U.S.A.

Thorns:

*Quantity.*—On main stalks from base—ordinary. On laterals—ordinary.

*Form.*—Broad base.

*Color (when young).*—Fern Green, Plate 0862.

*Position.*—Irregular.

Prickles:

*Quantity.*—On main stalks—few. On laterals—few.

I claim:

1. A new and distinct variety of rose plant of the hybrid tea class, substantially as herein shown and described, characterized particularly as to novelty by the unique combination of a vigorous, upright and well-branched plant habit, an abundance of dark green, glossy foliage which is relatively resistant to blackspot and powdery mildew, large, double flowers having from 60 to 70 petals and which open to a high-centered flower form, and a distinctive and attractive light red general color tonality of the flowers, with the color being lighter in shade on the reverse sides of the petals than on their upper sides.

No references cited.

ROBERT E. BAGWILL, Primary Examiner